(12) United States Patent
Moromugi

(10) Patent No.: US 11,363,967 B2
(45) Date of Patent: Jun. 21, 2022

(54) MUSCLE CONTRACTION DETECTION SENSOR

(71) Applicant: CHUO UNIVERSITY, Hachioji (JP)

(72) Inventor: Shunji Moromugi, Tokyo (JP)

(73) Assignee: CHUO UNIVERSITY, Hachioji (JP)

( * ) Notice: Subject to any disclaimer, the term of this patent is extended or adjusted under 35 U.S.C. 154(b) by 355 days.

(21) Appl. No.: 16/500,485

(22) PCT Filed: Apr. 2, 2018

(86) PCT No.: PCT/JP2018/014108
§ 371 (c)(1),
(2) Date: Oct. 3, 2019

(87) PCT Pub. No.: WO2018/186348
PCT Pub. Date: Oct. 11, 2018

(65) Prior Publication Data
US 2020/0289031 A1    Sep. 17, 2020

(30) Foreign Application Priority Data
Apr. 4, 2017    (JP) .............................. JP2017-074758

(51) Int. Cl.
*A61B 5/11*        (2006.01)
*A61B 5/22*        (2006.01)
(Continued)

(52) U.S. Cl.
CPC .......... *A61B 5/1107* (2013.01); *A61B 5/1036* (2013.01); *A61B 5/22* (2013.01);
(Continued)

(58) Field of Classification Search
CPC ............ A61B 5/22–228; A61B 5/1107; A61B 2562/168; A61B 5/03–038;
(Continued)

(56) References Cited

U.S. PATENT DOCUMENTS

| | | | | |
|---|---|---|---|---|
| 4,584,625 A | * | 4/1986 | Kellogg | ................. B25J 13/084 |
| | | | | 361/283.1 |
| 7,090,647 B2 | * | 8/2006 | Mimura | ............... A61B 5/1126 |
| | | | | 600/587 |
| 10,816,417 B2 | * | 10/2020 | Taniguchi | .............. B25J 13/081 |

FOREIGN PATENT DOCUMENTS

| | | | |
|---|---|---|---|
| JP | 2000111420 A | 4/2000 | |
| JP | 5107979 B2 | 12/2012 | |

(Continued)

OTHER PUBLICATIONS

Apr. 24, 2018, International Search Report issued in the International Patent Application No. PCT/JP2018/014108.

(Continued)

*Primary Examiner* — David J. McCrosky
(74) *Attorney, Agent, or Firm* — Kenja IP Law PC

(57) ABSTRACT

A muscle contraction detection sensor for detecting a muscle contraction that includes: a substrate to be mounted facing a muscle to be detected; at least two pressing members that are disposed on the substrate and are to be pressed against the muscle; and at least two reaction force detection units configured to detect respective reaction forces received by the pressing members, wherein the pressing members include a first pressing member and a second pressing member, the reaction force detection units include a first reaction force detection unit and a second reaction force detection unit, a muscle contraction is detected based on a change in a difference between, or a change in ratios of, the reaction force received by the first pressing member detected by the first reaction force detection unit and the reaction force received by the second pressing member detected by the second reaction force detection unit.

18 Claims, 5 Drawing Sheets

(51) Int. Cl.
*A61B 90/00* (2016.01)
*G01L 1/02* (2006.01)
*A61B 5/103* (2006.01)

(52) U.S. Cl.
CPC .......... *G01L 1/02* (2013.01); *A61B 2090/064* (2016.02); *A61B 2562/02* (2013.01); *A61B 2562/0247* (2013.01); *A61B 2562/164* (2013.01)

(58) Field of Classification Search
CPC ... A61B 5/1036; A61B 5/1038; A61B 5/6843; A61B 5/6885; A61B 2090/064; A61B 2090/065; A61B 2562/0247; G01L 1/02; G01L 1/083; G01L 2009/0067
See application file for complete search history.

(56) References Cited

FOREIGN PATENT DOCUMENTS

| JP | 2015120238 A | 7/2015 |
| JP | 5948325 B2 | 7/2016 |

OTHER PUBLICATIONS

Oct. 8, 2019, International Preliminary Report on Patentability issued in the International Patent Application No. PCT/JP2018/014108.

* cited by examiner

MUSCLE CONTRACTION DETECTION SENSOR

TECHNICAL FIELD

The present disclosure relates to a muscle contraction detection sensor configured to detect a muscle contraction.

BACKGROUND

Conventionally, wearable motion-assist apparatuses such as power assist suits (robot suits) and electric power gloves used in, for example, the medical field, a welfare field and the like are equipped with sensors configured as man-machine interfaces for detecting muscle contractions of users.

For example, PTL 1 set forth below describes a wearable motion-assist apparatus that includes a myoelectric potential sensor to be attached to a user and controls an operation of a driving unit of the motion-assist apparatus based on a changing amount of muscle constructions detected by the myoelectric potential sensor.

CITATION LIST

Patent Literature

PTL 1: JP-A-2015-120238

SUMMARY

Technical Problem

Generally, in order to attach the myoelectric potential sensor to a user, three electrodes need to be directly attached to the human. For stable attachment, a specific gel must be applied to the skin before the attachment of the electrodes. Further, each of the electrodes must be accurately attached to a predetermined site in order to ensure the detection accuracy. Thus, there is a problem that an attaching work of the wearable motion-assist apparatus is disadvantageously complicated for the daily use.

In view of the above problem, the present disclosure aims to provide a muscle contraction detection sensor that can be readily attached to a user.

Solution to Problem

A muscle contraction detection sensor according to the present disclosure is a muscle contraction detection sensor for detecting a muscle contraction and includes: a substrate to be mounted facing a muscle to be detected; at least two pressing members that are arranged on the substrate, are to be pressed against the muscle, and receive respective reaction forces that are caused by pressing and different from each other; and at least two reaction force detection units configured to detect the respective reaction forces received by the pressing members. The pressing members include a first pressing member and a second pressing member that receives the reaction force that is caused by the pressing against the muscle and smaller than the reaction force received by the first pressing member. The reaction force detection units include a first reaction force detection unit configured to detect the reaction force received by the first pressing member and the second reaction force detection unit configured to detect the reaction force received by the second pressing member. The muscle contraction detection sensor detects a muscle contraction based on a change in a difference between, or a change in ratios of, the reaction force received by the first pressing member detected by the first reaction force detection unit and the reaction force received by the second pressing member detected by the second reaction force detection unit.

Preferably, in the muscle contraction detection sensor according to the present disclosure configured as described above, the second pressing member is formed into an annular protruding shape that surrounds the first pressing member. Here, "the second pressing member is formed into an annular protruding shape that surrounds the first pressing member" encompasses various manners of surrounding the periphery of the first pressing member, including a case in which the second pressing member is formed to continuously surround the entire periphery of the first pressing member without a gap, a case in which the second pressing member is formed as a plurality of separated portions intermittently arranged around the first pressing member, and a case in which the second pressing member is formed into a C-shape having a cutout portion. Also, the "annular" shape encompasses various shapes including a circular (annular) shape, a rectangular shape, and a polygonal shape that surround the first pressing member, in addition to the circular shape (the annular shape).

Preferably, in the muscle contraction detection sensor according to the present disclosure configured as described above, the second pressing member is formed into a flexible bag-like shape that encapsulates a fluid.

Preferably, in the muscle contraction detection sensor according to the present disclosure configured as described above, the first pressing member is formed into a flexible bag-like shape that encapsulates a fluid.

Preferably, in the muscle contraction detection sensor according to the present disclosure configured as described above, the first pressing member is formed into a protruding shape with a circular cross-section, and the second pressing member is formed into an annular protruding shape that surrounds the first pressing member.

Preferably, in the muscle contraction detection sensor according to the present disclosure configured as described above, the first pressing member and the second pressing member are formed on a cover member that is detachably attached to the substrate.

Preferably, in the muscle contraction detection sensor according to the present disclosure configured as described above, the fluid is air.

Preferably, in the muscle contraction detection sensor according to the present disclosure configured as described above, a protruding height of the first pressing member from the substrate in an unloaded state is higher than a protruding height of the second pressing member from the substrate in an unloaded state.

Preferably, in the muscle contraction detection sensor according to the present disclosure configured as described above, the first reaction force detection unit is arranged between the substrate and the first pressing member, and the second reaction force detection unit is arranged between the substrate and the second pressing member.

Preferably, in the muscle contraction detection sensor according to the present disclosure configured as described above, the substrate includes an amplifier circuit incorporated therein, the amplifier circuit being configured to amplify and output detection signals input from the first reaction force detection unit and the second reaction force detection unit.

Advantageous Effect

The present disclosure can provide a muscle contraction detection sensor that can be readily attached to a user.

DETAILED DESCRIPTION

Hereinafter, an embodiment of the present disclosure will be described in detail with reference to the accompanying drawings.

Figure 1:
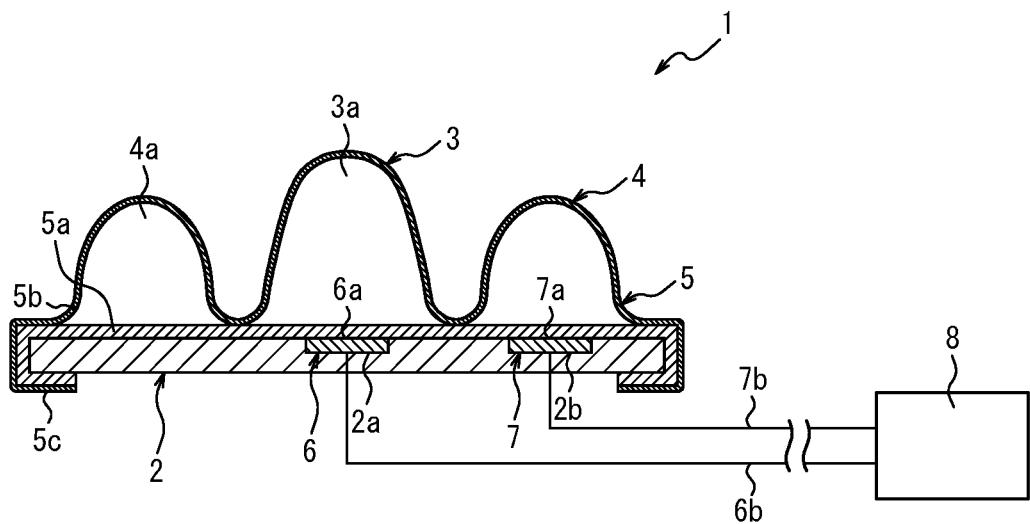
FIG. 1 is a cross-sectional diagram of a muscle contraction detection sensor according to an embodiment of the present disclosure.
Figure 2:
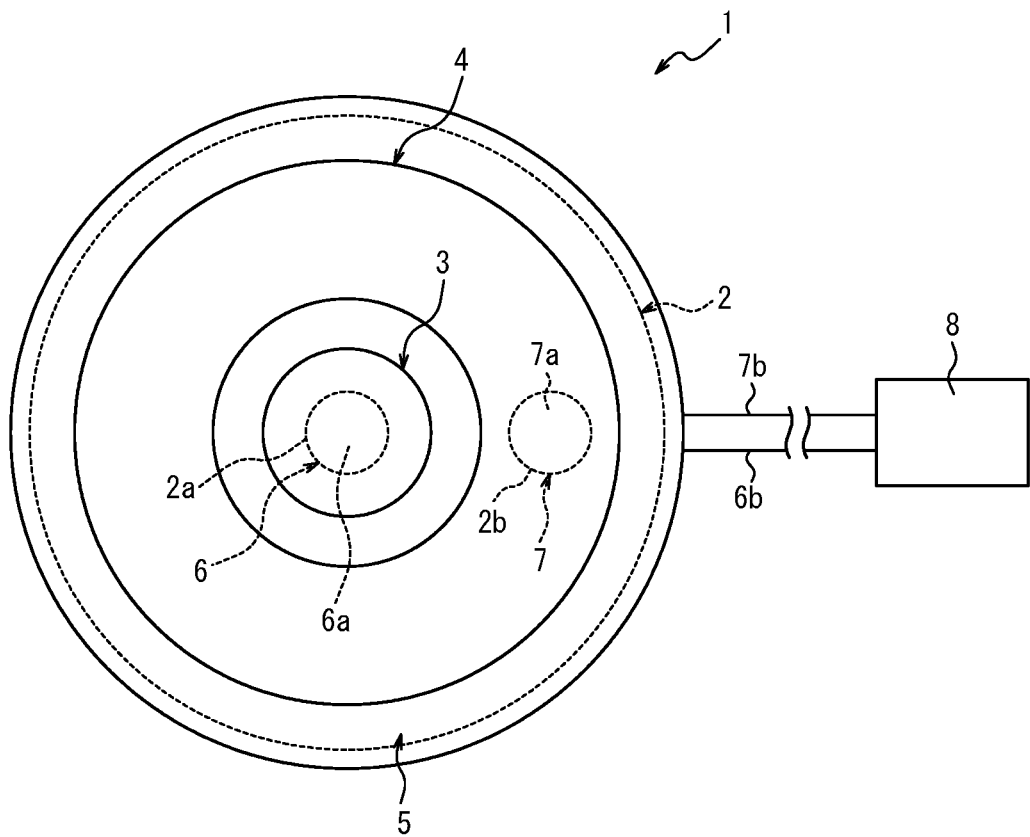
FIG. 2 is a plan view of the muscle contraction detection sensor illustrated in FIG. 1.

A muscle contraction detection sensor 1 according to an embodiment of the present disclosure illustrated in FIG. 1 and FIG. 2 is configured to be attached to a part of a human body such as an arm, a leg, and a torso and to detect a muscle contraction in the part. The muscle contraction detection sensor 1 can be used as, for example, man-machine interface that enables input to a wearable motion-assist apparatus such as a power assist suit and an electric power glove that are used in the medical field, the welfare field, and the like.

The muscle contraction detection sensor 1 is not limited to the man-machine interface of the motion-assist apparatus as described above and can be used for various applications that require detection of a muscle contraction.

The muscle contraction detection sensor 1 includes a substrate 2. The substrate 2 is to be directed to and mounted on a muscle to be detected and fixed to the human body in a state being biased to the muscle by an elastic belt or the like.

Preferably, the substrate 2 is formed into a disc-like shape with a diameter corresponding to a streak width (i.e., a width vertical to a stretching direction) of the muscle by the muscle contraction detection sensor 1. In the present embodiment, the diameter of the substrate 2 is 32 mm. The substrate 2 may be formed from a synthetic resin material such as engineering plastic or a metal material such as brass, and preferably has rigidity to the extent that excessive deformation thereof does not occur during use.

The diameter of the substrate 2 may be varied based on a muscle to be detected. Also, the shape of the substrate 2 is not limited to the disc-like shape and may have various shapes including, for example, a rectangular shape.

A first pressing member 3 and a second pressing member 4 are arranged on a top surface of the substrate 2 positioned on the upper side in FIG. 1. Each of the first pressing member 3 and the second pressing member 4 protrudes from the top surface of the substrate 2, and pressed against the muscle when the substrate 2 is biased to the muscle by an elastic belt or the like and fixed to the human body. That is, when the muscle contraction detection sensor 1 is attached to the human body, the first pressing member 3 and the second pressing member 4 are directly, or via a cloth or the like, pressed against the skin in a part of the human body that includes the muscle.

In the present embodiment, the first pressing member 3 and the second pressing member 4 are formed on a cover member 5 that is detachably attached to the substrate 2. The cover member 5 has a configuration in which a thin top sheet 5b is attached to a surface of a thin substrate sheet 5a by means of heat welding or an adhesive. The substrate sheet 5a is formed from, for example, a synthetic resin material such as vinyl chloride or the like and has a circular shape with a diameter larger than the substrate 2. The top sheet 5b is also formed from a synthetic resin material such as vinyl chloride or the like and has protrusions corresponding to the first pressing member 3 and the second pressing member 4.

Figure 3:
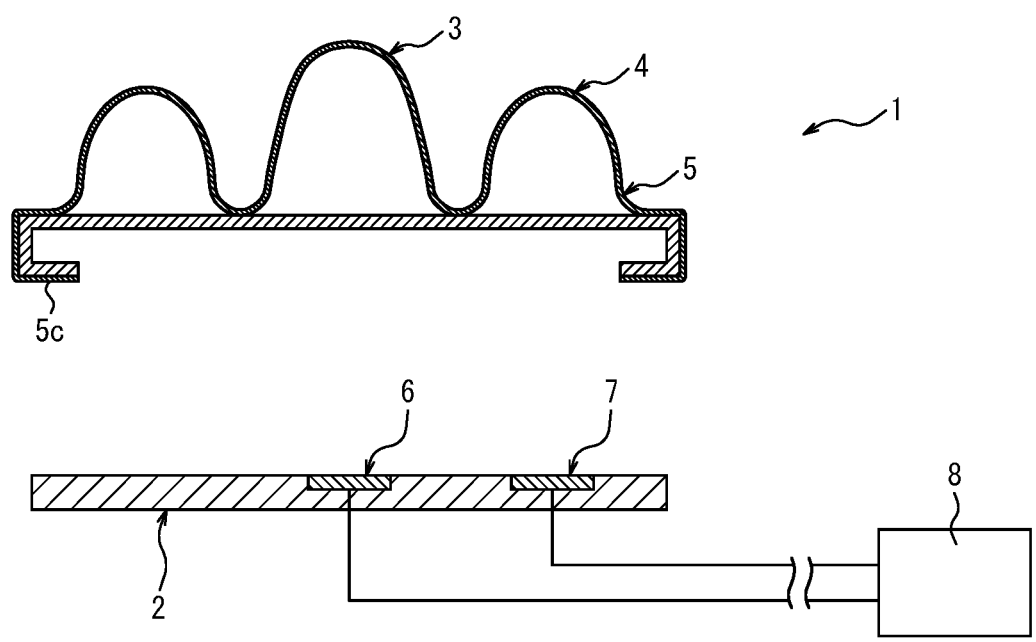
FIG. 3 is an exploded diagram illustrating a state in which a cover member is removed from a substrate.

The cover member 5 is attached to the substrate 2 in such a manner that the substrate sheet 5a is positioned on the top surface of the substrate 2 and a folded portion 5c formed at the outer periphery of the cover member 5 covers the outer periphery of the substrate 2. The cover member 5 can be removed from the substrate 2 by removing the folded portion 5c from the outer periphery of the substrate 2 as illustrated in FIG. 3. In this way, the cover member 5 is detachably attached to the substrate 2.

This configuration enables the cover member 5 to have a configuration that is inexpensive and can be readily manufactured simply by bonding two sheets together, reducing the manufacturing cost of the muscle contraction detection sensor 1. Also, by virtue of the inexpensive and disposable configuration of the cover member 5, when the first pressing member 3 or the second pressing member 4 is damaged or becomes dirty, the first pressing member 3 and the second pressing member 4 may be easily replaced simply by attaching a new cover member 5. Further, the configuration of the muscle contraction detection sensor 1 can be simplified and can reduce the cost.

Note that the folded portion 5c may be formed into a gathered shape or may include a rubber band attached to the inner peripheral edge thereof, such that the cover member 5 is not likely to come off the substrate 2 and easily detached from the substrate 2. An attachment structure of the cover member 5 to the substrate 2 is not limited to the folded portion 5c described above and may employ various manners.

In the above configuration as illustrated in FIG. 1, the first pressing member 3 is formed into a flexible bag-like shape such that an internal space 3a is defined between the substrate 5a and the top sheet 5b and encapsulates a fluid (air in this embodiment). The first pressing member 3 has a protruding shape that includes a rounded upper end (top end) and a circular cross-section (a cross-section parallel to the top surface of the substrate 2). The first pressing member 3 is arranged on the substrate 2 in a manner coaxial therewith and protrudes from the top surface by a predetermined protruding height.

In the present embodiment, the second pressing member 4 is also formed into a bag-like shape that encapsulates a fluid. In particular, the second pressing member 4 is formed into a flexible bag-like shape such that an internal space 4a is defined between the substrate 5a and the top sheet 5b and encapsulates a fluid (air in this embodiment). In the present embodiment, the second pressing member 4 is formed into an annular protruding shape that surrounds the first pressing member 3. In particular, the second pressing member 4 is formed into a protruding shape that has an annular shape as a whole and includes a curved top surface, and arranged being coaxial with the substrate 2 in such a manner as to surround the periphery of the first pressing member 3. In the present embodiment, the second pressing member 4 is formed into an annular shape as a whole. In the present embodiment, also, the second pressing member 4 is formed into a shape that continuously surrounds the entire periphery of the first pressing member 3 without a gap. The second pressing member is not limited to the annular shape that continuously surrounds the entire periphery of the first pressing member without a gap, and may have any shape that is arranged surrounding the periphery of the first pressing member 3 including, for example, a shape configured as a plurality of separated portions intermittently arranged around the first pressing member or a C-shape having a cutout portion. The second pressing member 4 is not limited to the annular shape that surrounds the periphery of the first pressing member 3 in the circular shape in a plan view and may have various shapes including, for example, a rectangular shape or a polygonal shape that surrounds the first pressing member 3 in a plan view.

Although each of the internal space 3a of the first pressing member 3 and the internal space 4a of the second pressing member 4 encapsulates air as a fluid, this is not restrictive. For example, a compressible fluid (gas) other than air or an incompressible fluid such as water may be encapsulated. However, it is preferable to encapsulate air in the internal space 3a of the first pressing member 3 and in the internal space 4a of the second pressing member 4, from the view point of cost reduction of the muscle contraction detection sensor 1.

In an unloaded state, i.e., in a natural state in which the first pressing member 3 and the second pressing member 4 are not pressed against a muscle, the protruding height of the first pressing member 3 from the top surface of the substrate 2 is higher than the protruding height of the second pressing member 4 from the top surface of the substrate 2, as can be seen from FIG. 1. Note that the pressure in the internal space 3a of the first pressing member 3 and the pressure in the internal space 4a of the second pressing member 4 are equal to each other in the unloaded state.

As described above, by virtue of the annular protruding shape of the second pressing member 4 that surrounds the first pressing member 3, when the muscle contraction detection sensor 1 is attached to the predetermined part of the human body, the second pressing member 4 can stably support the substrate 2 at the predetermined part of the human body. Especially when the second pressing member 4 is formed into the annular shape that continuously surrounds the entire periphery of the first pressing member 3 without a gap, the second pressing member 4 can support the substrate 2 at the predetermined part of the human body in a more stable manner. Thus, the substrate 2 can be pressed against the muscle in a stable manner without a large tilt from its orientation facing the muscle. Also, by reducing the tilt of the substrate 2, the substrate 2 can be inhibited from directly contacting the human body, and the muscle contraction detection sensor 1 can more accurately detect a muscle contract.

Further, by virtue of the flexible bag-like shapes of the first pressing member 3 and the second pressing member 4, the pressing members 3 and 4 are flexibly deformed and uniformly apply pressures when pressed against a muscle of the human body. Thus, the comfort for the human body is improved. That is, the flexible bag-like shapes can reduce the pain and discomfort given to the human body when the muscle contraction detection sensor 1 is attached to the human body for a long time period. Especially when the internal space 3a of the first pressing member 3 and the internal space 4a of the second pressing member 4 encapsulate a compressible fluid such as air, the pressing members 3 and 4 can become more flexible and improve the comfort for the human body when the pressing members 3 and 4 are pressed against a muscle of the human body. Thus, muscle contraction detection sensor 1 can improve a wearing feeling and comfortability when attached to the human body.

A first reaction force detection unit 6 is provided to the substrate 2 and configured to detect a reaction force (a pressure) applied to the first pressing member 3 by the human body when the first pressing member 3 is directed to the muscle and pressed against the human body. In the present embodiment, the first reaction force detection unit 6 is configured as a pressure sensor having disc-like shape. The first reaction force detection unit 6 is attached to the substrate 2 in a state being fitted into a first circular groove 2a formed in the central axial position of the top surface of the substrate 2, and includes a pressure detection surface 6a that is exposed and flush with the top surface of the substrate 2. That is, the first reaction force detection unit 6 is arranged between the substrate 2 and the first pressing member 3.

A second reaction force detection unit 7 is provided to the substrate 2 and configured to detect a reaction force (a pressure) applied to the second pressing member 4 by the human body when the second pressing member 4 is directed to the muscle and pressed against the human body. In the present embodiment, the second reaction force detection unit 7 is also configured as a pressure sensor having a disc-like shape. The second reaction force detection unit 7 is attached to the substrate 2 in a state being fitted into a second circular groove 2b formed at a position on the top surface of the substrate 2 immediately under (corresponding to a radial center position of) the second pressing member 4. A pressure detection surface 7a of the second reaction force detection unit 7 is also exposed and flush with the top surface of the substrate 2. Thus, the second reaction force detection unit 7 is arranged between the substrate 2 and the second pressing member 4. Because of the configuration of this embodiment in which the second pressing member 4 includes the internal space 4a that encapsulates air, even when only a portion of the second pressing member 4 receives a reaction force from the human body, the pressure in the internal space 4a increased by receiving the reaction force is transmitted to the entire second pressing member 4 through the air. Thus, a change in the pressure can be accurately detected by the second reaction force detection unit 7 alone.

By virtue of the bag-like shape of the second pressing member 4 encapsulating air as described above in the present embodiment, even when the second pressing member 4 is formed into an annular protruding shape, the second reaction force detection unit 7 alone can detect a reaction force (a pressure) applied to the second pressing member 4. Thus, cost of the muscle contraction detection sensor 1 can be reduced. In a case in which the second pressing member 4 is configured as a plurality of separated portions intermittently arranged along the circumferential direction around the first pressing member 3 as described above, each of the separated portions of the second pressing member 4 may be connected to one another via a tube or the like to have a uniform internal pressure. Thus, the second reaction force detection unit 7 alone can detect a reaction force (a pressure) applied to the second pressing member 4 by the human body.

Alternatively, in the case in which the second pressing member 4 is configured as a plurality of separated portions intermittently arranged along the circumferential direction around the first pressing member 3, a plurality of second reaction force detection units 7 corresponding to the respective separated portions of the second pressing member 4 may be provided to detect respective reaction forces (pressures) applied to the second pressing member 4 by the human body.

Each of the first reaction force detection unit 6 and the second reaction force detection unit 7 may be configured as, for example, a strain gauge pressure transducer. Other than the strain gauge pressure transducer, each of the first reaction force detection unit 6 and the second reaction force detection unit 7 may be configured as a pressure sensor of any type that can detect reaction forces received by the first pressing member 3 and the second pressing member 4 and output the detected reaction forces as electrical signals or the like.

The first reaction force detection unit 6 and the second reaction force detection unit 7 are connected to a determination unit 8 via a wiring 6b and a wiring 7b, respectively. The determination unit 8 may be incorporated into a controller of an apparatus having the muscle contraction detection sensor 1 applied thereto. For example, when the muscle contraction detection sensor 1 is used as a man-machine interface that enables input to the wearable motion-assist apparatus such as a power assist suit or an electric power glove, the determination unit 8 is configured as one functional element and incorporated into the controller (not illustrated) of the wearable motion-assist apparatus.

The determination unit 8 detects a contraction of the muscle, based on a change in a difference between, or a change in ratios of, a detection signal input from the first reaction force detection unit 6 and a detection signal input from the second reaction force detection unit 7, i.e., a reaction force applied to the first pressing member 3 by the human body and a reaction force applied to the second pressing member 4 by the human body. A method for detecting a muscle contraction will be described in detail later.

Figure 4A:
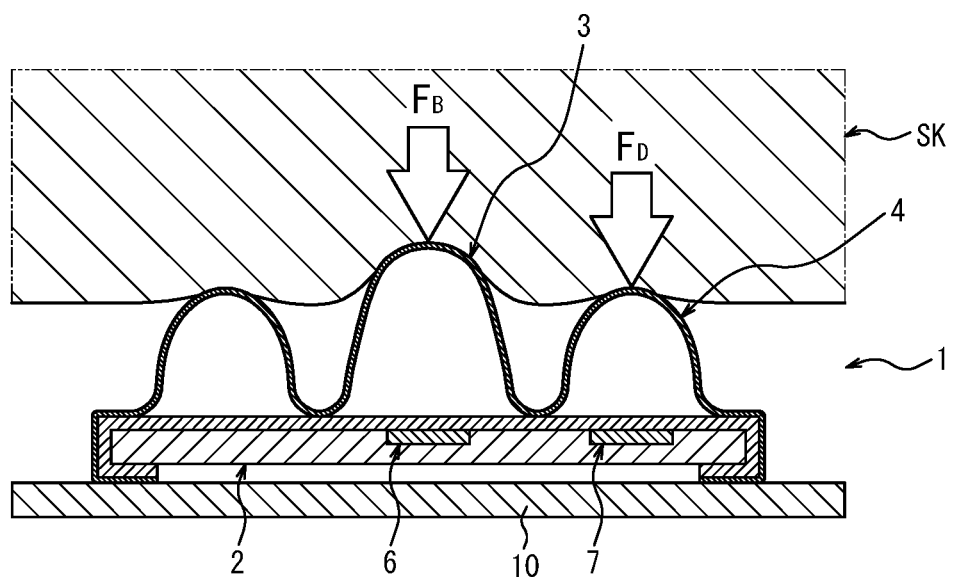
FIG. 4A is a cross-sectional diagram illustrating a state in which the muscle contraction detection sensor is attached to a human body.

FIG. 4A is a cross-sectional diagram illustrating a state of the muscle contraction detection sensor 1 described above attached to the human body, and FIG. 4B is a cross-sectional diagram illustrating a state of the muscle contraction detection sensor 1 described above when the muscle contracts. Next, the method for detecting a contraction of the muscle using the muscle contraction detection sensor 1 will be described.

As illustrated in FIG. 4A, the muscle contraction detection sensor 1 is attached to the predetermined part of the human body using, for example, an elastic belt 10. That is, the muscle contraction detection sensor 1 is directed such that the substrate 2 is directed to the muscle (not illustrated) and the first pressing member 3 and the second pressing member 4 face the muscle on the opposite side from the substrate 2, and attached to the predetermined part of the human body in a state being held between the elastic belt 10 wound around the human body and the human body. When the muscle contraction detection sensor 1 is attached to the predetermined part of the human body, the first pressing member 3 and the second pressing member 4 face the muscle and are pressed against the human body by the elastic force of the elastic belt 10.

The elastic belt 10 is a member that can generate a tension capable of pressing the muscle contraction detection sensor 1 against the predetermined part of the human body, avoiding excessive deformation of the substrate 2, the first pressing member 3, and the second pressing member 4. Also, the muscle contraction detection sensor 1 may be fixed to the predetermined part of the human body using another member such as a corset or a supporter, other than the elastic belt 10.

When the muscle contraction detection sensor 1 is attached to the predetermined part of the human body, the first pressing member 3 and the second pressing member 4 may be directly pressed against the skin SK of the human body, or via a cloth, towel, or the like arranged between the first and second pressing members 3 and 4 and the skin SK. FIG. 4A, FIG. 4B, and FIGS. 5A to 4C illustrate respective states in which the first pressing member 3 and the second pressing member 4 are directly pressed against the skin SK of the human body.

As illustrated in FIG. 4A, in a state in which the muscle contraction detection sensor 1 is attached to the predetermined part of the human body and the first pressing member 3 and the second pressing member 4 are directed to the muscle and pressed against the human body, each of the first pressing member 3 and the second pressing member 4 is slightly deformed by a reaction force from the skin SK of the human body. In this state also, the protruding height of the first pressing member 3 from the top surface of the substrate 2 is higher than the protruding height of the second pressing member 4 from the top surface of the substrate 2, in a manner similar to the natural state.

At this time, because the skin SK flexibly bends and contacts both the first pressing member 3 and the second pressing member 4, a reaction force $F_B$ is applied to the first pressing member 3 by the skin SK, and a reaction force $F_D$ is applied to the second pressing member 4 by the skin SK. The reaction force $F_B$ and the reaction force $F_D$ are detected by the first reaction force detection unit 6 and the second reaction force detection unit 7, respectively, and input to the determination unit 8. In the pressing state as described above, because the protruding height of the first pressing member 3 from the top surface of the substrate 2 is higher than the protruding height of the second pressing member 4 from the top surface of the substrate 2, the reaction force $F_B$ applied to the first pressing member 3 by the human body is greater than the reaction force $F_D$ applied to the second pressing member 4 by the human body. The determination unit 8 detects a contraction of the muscle based on a change in a difference between, or a change in ratios of, the reaction force $F_B$ and the reaction force $F_D$ input to the determination unit 8.

In the present embodiment, in order to more accurately detect a muscle contraction, the determination unit 8 acquires a parameter value S indicating a degree of a muscle contraction by calculating a total $F_T$ of the reaction force $F_B$ applied to the first pressing member 3 by the human body and the reaction force $F_D$ applied to the second pressing member 4 by the human body and then dividing the reaction force $F_B$ by the total $F_T$. The below equation (1) is used for the calculation of the parameter value S. The parameter value S is a dimensionless variable that varies within a range of 0 to 1.

$$S=F_B/(F_B+F_D)=F_B/F_T \qquad \text{Equation (1)}$$

The determination unit 8 calculates the parameter value S in the state illustrated in FIG. 4A as a reference value and detects a muscle contraction based on a change in the parameter value S from the reference value. Here, the parameter value S is a value that varies following a change in the ratios of the reaction force $F_B$ applied to the first pressing member 3 and the reaction force $F_D$ applied to the second pressing member 4. Thus, detecting a muscle contraction based on a change in the parameter value S corresponds to detecting a muscle contraction based on a change in the ratios of the reaction force $F_B$ applied to the first pressing member 3 and the reaction force $F_D$ applied to the second pressing member 4. Note that the determination unit 8 may detect a muscle contraction based on a change in the difference between the reaction force $F_B$ applied to the first pressing member 3 and the reaction force $F_D$ applied to the second pressing member 4, rather than detecting a muscle contraction based on a change in the ratios of the reaction force $F_B$ applied to the first pressing member 3 and the reaction force $F_D$ applied to the second pressing member 4.

Figure 4B:
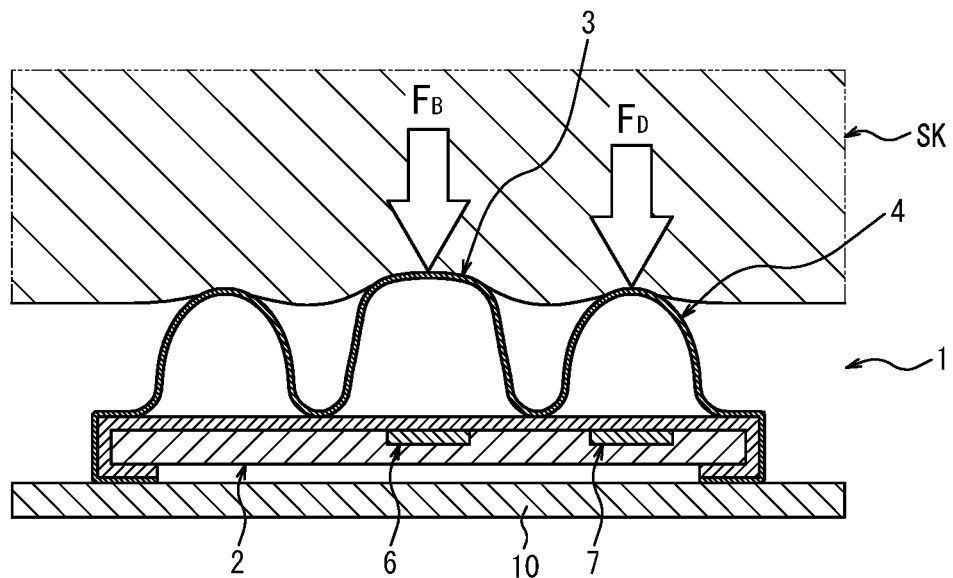
FIG. 4B is a cross-sectional diagram illustrating a state of the muscle contraction detection sensor when a muscle contracts.

When the muscle gradually contracts and hardens from the state illustrated in FIG. 4A, the skin SK strongly contacts and elastically deforms the first pressing member 3 that has a higher protruding height from the substrate 2, while gradually separating from the second pressing member 4. Thus, the ratio of the reaction force $F_B$ to the total $F_T$ gradually increases following the muscle contraction, whereas the ratio of the reaction force $F_D$ to the total $F_T$ gradually decreases. That is, the parameter S gradually increases approaching the reference value as following the muscle contraction. When the muscle further contracts, the skin SK strongly contacts and elastically deforms the first pressing member 3 as illustrated in FIG. 4B while lightly contacting the skin S, and the parameter value S becomes close to 1. When the muscle further contracts, the skin SK contacts the first pressing member 3 alone, and the parameter value S becomes 1. As described above, the parameter value S increases from the reference value to 1, following the muscle contraction. Thus, the determination unit 8 can detect a muscle contraction based on an increase in the parameter value S and also detect a degree of muscle contraction based on the parameter value S at a corresponding time.

On the other hand, when the muscle relaxes and the contraction is eliminated from the state illustrated in FIG. 4B, the ratio of the reaction force $F_B$ to the total $F_T$ gradually decreases, and the parameter value S gradually decreases from 1 to the reference value. Thus, the determination unit 8 can detect the muscle relaxation based on the decrease in the parameter value S, and also detect a degree of muscle relaxation based on the parameter value S at a corresponding time.

The parameter value S may be expressed by, for example, $S=F_D (F_B F_D)=F_D/F_T$. In this case, the parameter value S gradually decreases following the muscle contraction. Thus, the determination unit 8 can detect a muscle contraction based on a decrease in the parameter value S.

As described above, the muscle contraction detection sensor 1 according to the present disclosure detects a muscle contraction, that is, whether a muscle is contracting, based on a change in the difference between, or a change in the ratios of, the reaction force $F_B$ applied to the first pressing member 3 and the reaction force $F_D$ applied to the second pressing member 4. This configuration eliminates the necessity to accurately detect the values of the reaction forces $F_B$ and $F_D$. Thus, the muscle contraction detection sensor 1 can accurately detect a muscle contraction even in a state being attached to the human body via a cloth, a towel, or the like. Thus, the muscle contraction detection sensor 1 has less usage restrictions and can be readily attached to the predetermined part of the human body that includes the muscle, using the elastic belt 10 or the like. Accordingly, the muscle contraction detection sensor 1 enables easy attachment of a wearable motion-assist apparatus for a daily use.

A myoelectric potential sensor may detect a muscle contraction by mistake, depending on an attaching position of an electrode. However, the muscle contraction detection sensor 1 of the present disclosure detects a physical change in a particular muscle (a change in hardness of the muscle following a muscle contraction) and thus can accurately detect the muscle contraction (a muscle activity). Further, the muscle contraction detection sensor 1 of the present disclosure can detect more minor muscle contractions, as compared to the myoelectric potential sensor.

The muscle contraction detection sensor 1 of the present disclosure can accurately detect a muscle contraction without being affected by fatigue, unlike a myoelectric potential sensor, and accurately detect a muscle contraction caused by a functional electrical stimulation.

Also, the muscle contraction detection sensor 1 of the present disclosure can eliminate the influence of external forces and thus can obtain high robustness against the external forces. Thus, the muscle contraction detection sensor 1 can more accurately detect a muscle contraction.

Further, the muscle contraction detection sensor 1 of the present disclosure has a simple configuration that enables mass-production thereof at low cost.

Figure 5A:
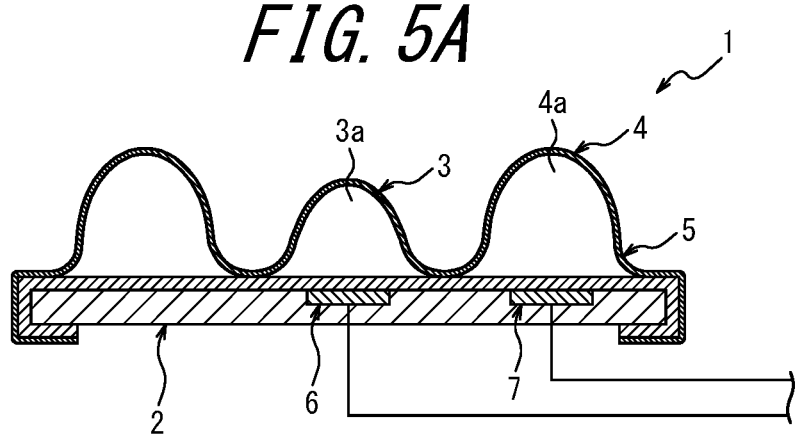
FIG. 5A to FIG. 5C are diagrams illustrating respective example variations of the muscle contraction detection sensor illustrated in FIG. 1.
Figure 5B:
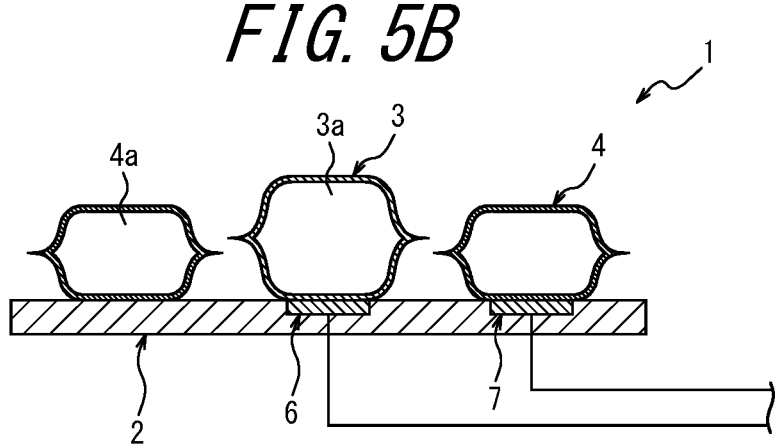
Figure 5C:
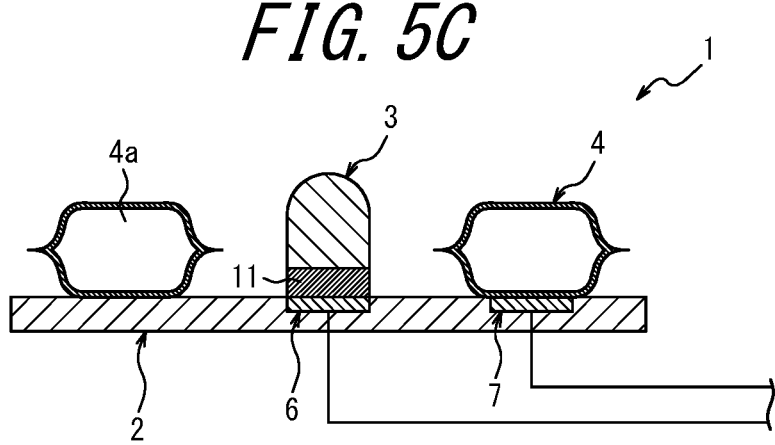

FIGS. 5A to 5C illustrate cross-sectional diagrams of respective example variations of the muscle contraction detection sensor 1 illustrated in FIG. 1. Members illustrated in FIGS. 5A to 5C corresponding to those in the above description are denoted by the common reference signs.

In the case illustrated in FIG. 1, the first pressing member 3 is formed into the protruding shape having the circular cross-section, and the second pressing member 4 is formed into the annular shape that surrounds the first pressing member 3. Also, the protruding height of the first pressing member 3 from the top surface of the substrate 2 is higher than the protruding height of the second pressing member 4 from the top surface of the substrate 2. Thus, when the muscle contraction detection sensor 1 is attached to the predetermined part of the human body, the reaction force $F_B$ applied to the first pressing member 3 by the human body is greater than the reaction force $F_D$ applied to the second pressing member 4 by the human body. However, the muscle contraction detection sensor 1 may be configured as described in the example variation illustrated in FIG. 5A in which the first pressing member 3 is formed into the protruding shape having the circular cross-section and the second pressing member 4 is formed into the annular shape that surrounds the first pressing member 3, and the protruding height of the first pressing member 3 from the top surface of the substrate 2 is lower than the protruding height of the second pressing member 4 from the top surface of the substrate 2 such that, when the muscle contraction detection sensor 1 is attached to the predetermined part of the human body, the reaction force $F_B$ applied to the first pressing member 3 by the human body is smaller than the reaction force $F_D$ applied to the second pressing member 4 by the human body. In this configuration, the second pressing member 4 having the protruding height higher than that of the first pressing member 3 can support the substrate 2 against the human body in a more stable manner.

Further, in the case illustrated in FIG. 1, the first pressing member 3 and the second pressing member 4 are integrally formed with the cover member 5. However, as described in the example variation of the muscle contraction detection sensor 1 illustrated in FIG. 5B, the first pressing member 3 and the second pressing member 4 may be separately formed and fixed to the top surface of the substrate 2 using an adhesive or the like. This configuration can suppress the reaction forces applied to the first pressing member 3 and the second pressing member 4 from being transmitted therebetween. Thus, the reaction forces applied to the first pressing member 3 and the second pressing member 4 can be detected more correctly, and thus a muscle contraction can be detected more accurately.

Further, in the case illustrated in FIG. 1, each of the first pressing member 3 and the second pressing member 4 are formed into the bag-like shapes that encapsulate air. However, as described in the example variation of the muscle contraction detection sensor 1 illustrated in FIG. 5C, the second pressing member 4 may be formed into the bag-like shape while the first pressing member 3 is formed from a soft material such as silicon and formed into a protruding shape having a semicircular top portion and a circular cross-section. In this case, a rubber sheet 11 is preferably arranged between the first pressing member 3 and the first reaction force detection unit 6. This configuration can facilitate the generation of a difference between the height of the first pressing member 3 and the height of the second pressing member 4 at the time of a muscle contraction and detect the muscle contraction more correctly. Also, because the first pressing member 3 is formed from a soft material such as silicone, the aforementioned effect may be obtained, and the comfort for the human body when the first pressing member 3 is directed to the muscle and pressed against the human body can be improved.

In the configuration illustrated in FIG. 5C, the first pressing member 3 that is made from a soft material such as silicon and formed into a protruding shape may be integrally formed with the second pressing member 4 and covered with a soft bag-like member encapsulating a fluid (air). In this configuration, the soft bag-like member contacts the human body when the first pressing member 3 is directed to the muscle and pressed against the human body. Thus, the comfort for the human body can be further improved.

Figure 6:
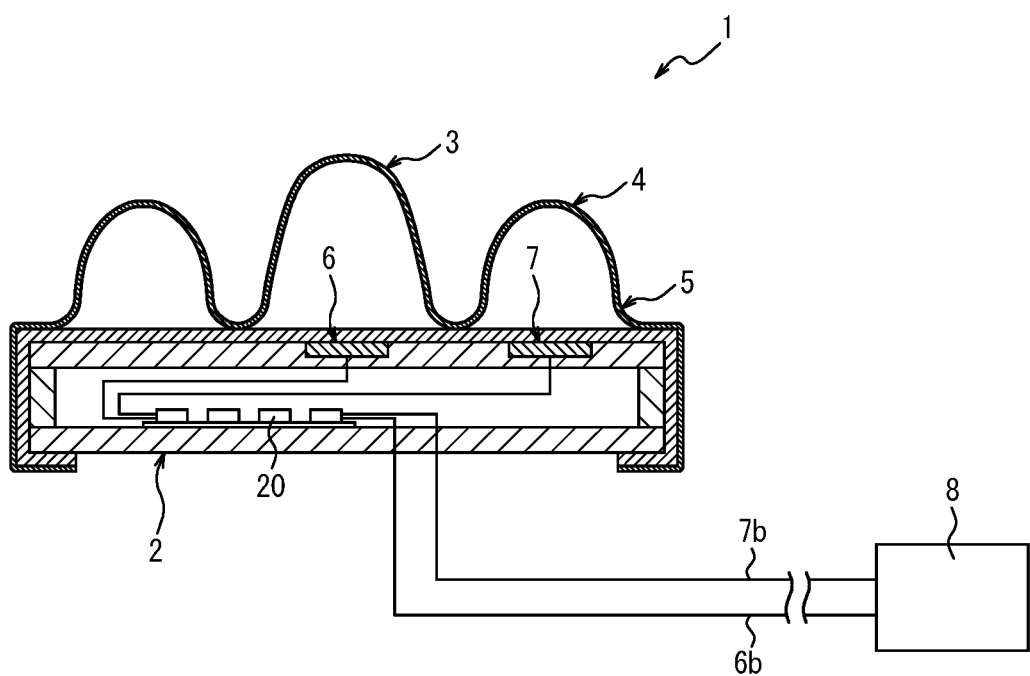
FIG. 6 is a cross-sectional diagram of an example variation of the muscle contraction detection sensor illustrated in FIG. 1.

FIG. 6 is a cross-sectional diagram of the muscle contraction detection sensor 1 illustrated in FIG. 1 according to an example variation. Members illustrated in FIG. 6 corresponding to the members described above are denoted by the common reference signs.

In the case illustrated in FIG. 1, the wiring 6b of the first reaction force detection unit 6 and the wiring 7b of the second reaction force detection unit 7 are directly drawn from the substrate 2 and connected to the determination unit 8. However, the muscle contraction detection sensor 1 may have a configuration illustrated in FIG. 6 in which an amplifier circuit 20 is built into the substrate 2 and configured to amplify detection signals input from the first reaction force detection unit 6 and the second reaction force detection unit 7 and output amplified detection signals to the determination unit 8, such that the detection signals input from the first reaction force detection unit 6 and the second reaction force detection unit 7 are input to the determination unit 8 via the amplifier circuit 20. In this case, the substrate 2 may include an internal space formed by a spacer arranged between a front plate member and a rear plate member, and the amplifier circuit 20 may be arranged in the internal space. This configuration can amplify detection signals output from the first reaction force detection unit 6 and the second reaction force detection unit 7 using the amplifier circuit 20 within the substrate 2 even when the detection signals are weak, and thus can reduce the influence on the detection signals from noise. The amplifier circuit 20 may be a circuit having a function to reduce noise components included in the detection signals, in addition to the function to amplify the detection signals. Alternatively, a noise reduction circuit (not illustrated) independent of the amplifier circuit 20 may be built into the substrate 2 in a manner similar to the amplifier circuit 20, or provided external to the substrate 2. The noise reduction circuit is connected between the first and second reaction force detection units 6 and 7 and the determination unit 8.

It should be appreciated that the present disclosure is not limited to the embodiment set forth above and may be modified in various manners without departing from the gist of the present disclosure.

For example, in the above embodiment the protruding height of the first pressing member 3 from the substrate 2 in the unloaded state is higher than the protruding height of the second pressing member 4 from the substrate 2 in the unloaded state. However, this is not restrictive. For example, the first pressing member 3 may have an elasticity or a resilience greater than that of the second pressing member 4 such that, regardless of the protruding height in the unloaded state, the reaction force applied to the first pressing member 3 by the human body in a pressing state being directed to and pressed against the muscle is greater than the reaction force applied to the second pressing member 4 by the human body. In this configuration, the protruding height of the first pressing member 3 from the substrate 2 in the unloaded state may be the same as, or lower than, the protruding height of the second pressing member 4 from the substrate 2 in the unloaded state.

Also, although the substrate 2 is formed into the disc-like shape in the above embodiment, the substrate 2 is not limited to this shape and may be formed into various shapes in accordance with a part of the human body that includes a muscle to be detected.

Further, although one second reaction force detection unit 7 is provided in the above embodiment, this is not restrictive. A plurality of second reaction force detection units 7 may be arranged at predetermined intervals in the circumferential direction, in order to more accurately detect the reaction force applied to the second pressing member 4.

REFERENCE SIGNS LIST 1 muscle contraction detection sensor
2 substrate
2a first circular groove
2b second circular groove
3 first pressing member
3a internal space
4 second pressing member
4a internal space
5 cover member
5a substrate sheet
5b top sheet
5c folded portion
6 first reaction force detection unit
6a pressure detection surface
6b wiring
7 second reaction force detection unit
7a pressure detection surface
7b wiring
8 determination unit
10 elastic belt
11 rubber sheet
20 amplifier circuit
SK skin

The invention claimed is:

1. A muscle contraction detection sensor for detecting a muscle contraction, the muscle contraction detection sensor comprising:
   a substrate to be mounted facing a muscle to be detected;
   at least two pressing members that are arranged on the substrate, the pressing members being configured to be pressed against the muscle, and receive respective reaction forces that are caused by pressing, and the respective reaction forces being different from each other; and
   at least two reaction force detection units configured to detect the respective reaction forces received by the pressing members,
   wherein the pressing members include a first pressing member and a second pressing member,
   the reaction force received by the second pressing member is smaller than the reaction force received by the first pressing member,
   the reaction force detection units include a first reaction force detection unit configured to detect the reaction force received by the first pressing member and a second reaction force detection unit configured to detect the reaction force received by the second pressing member,
   a muscle contraction is detected by calculating a change in a difference between, or a change in a ratio of, the reaction force received by the first pressing member detected by the first reaction force detection unit and the reaction force received by the second pressing member detected by the second reaction force detection unit,
   a protruding height of the first pressing member from the substrate in an unloaded state is larger than a protruding height of the second pressing member from the substrate in an unloaded state, and
   the first pressing member and the second pressing member are configured to receive the reaction force independently of each other.

2. The muscle contraction detection sensor according to claim 1,
   wherein the second pressing member is formed into an annular protruding shape that surrounds the first pressing member.

3. The muscle contraction detection sensor according to claim 1,
   wherein the second pressing member is formed into a flexible bag-like shape that encapsulates a fluid.

4. The muscle contraction detection sensor according to claim 3,
   wherein the first pressing member is formed into a flexible bag-like shape that encapsulates a fluid.

5. The muscle contraction detection sensor according to claim 4,
   wherein the first pressing member is formed into a protruding shape with a circular cross-section, and the second pressing member is formed into an annular protruding shape that surrounds the first pressing member.

6. The muscle contraction detection sensor according to claim 5,
   wherein the first pressing member and the second pressing member are formed on a cover member that is detachably attached to the substrate.

7. The muscle contraction detection sensor according to claim 3, wherein the fluid is air.

8. The muscle contraction detection sensor according to claim 1,
   wherein the first reaction force detection unit is arranged between the substrate and the first pressing member, and the second reaction force detection unit is arranged between the substrate and the second pressing member.

9. The muscle contraction detection sensor according to claim 1,
   wherein the substrate includes an amplifier circuit incorporated therein, the amplifier circuit being configured to amplify and output detection signals input from the first reaction force detection unit and the second reaction force detection unit.

10. A muscle contraction detection sensor for detecting a muscle contraction, the muscle contraction detection sensor comprising:
    a substrate to be mounted facing a muscle to be detected;
    at least two pressing members that are arranged on the substrate, the pressing members being configured to be pressed against the muscle to receive respective reaction forces that are caused by pressing, and the respective reaction force being different from each other; and
    at least two reaction force detection units configured to detect the respective reaction forces received by the pressing members,
    wherein the pressing members include a first pressing member and a second pressing member,
    the reaction force received by the second pressing member is smaller than the reaction force received by the first pressing member,
    the reaction force detection units include a first reaction force detection unit configured to detect the reaction force received by the first pressing member and a second reaction force detection unit configured to detect the reaction force received by the second pressing member,
    a muscle contraction is detected by calculating a change in a difference between, or a change in a ratio of, the reaction force received by the first pressing member detected by the first reaction force detection unit and the reaction force received by the second pressing member detected by the second reaction force detection unit, and
    the second pressing member is formed into an annular protruding shape that surrounds the first pressing member.

11. The muscle contraction detection sensor according to claim 10,
    wherein the second pressing member is formed into a flexible bag-like shape that encapsulates a fluid.

12. The muscle contraction detection sensor according to claim 11,
    wherein the first pressing member is formed into a flexible bag-like shape that encapsulates a fluid.

13. The muscle contraction detection sensor according to claim 12,
    wherein the first pressing member is formed into a protruding shape with a circular cross-section, and the second pressing member is formed into an annular protruding shape that surrounds the first pressing member.

14. The muscle contraction detection sensor according to claim 13,
    wherein the first pressing member and the second pressing member are formed on a cover member that is detachably attached to the substrate.

15. The muscle contraction detection sensor according to claim 11, wherein the fluid is air.

16. The muscle contraction detection sensor according to claim 10,
wherein a protruding height of the first pressing member from the substrate in an unloaded state is larger than a protruding height of the second pressing member from the substrate in an unloaded state.

17. The muscle contraction detection sensor according to claim 10,
wherein the first reaction force detection unit is arranged between the substrate and the first pressing member, and the second reaction force detection unit is arranged between the substrate and the second pressing member.

18. The muscle contraction detection sensor according to claim 10,
wherein the substrate includes an amplifier circuit incorporated therein, the amplifier circuit being configured to amplify and output detection signals input from the first reaction force detection unit and the second reaction force detection unit.

* * * * *